United States Patent [19]
Koerber, Sr. et al.

[11] Patent Number: 4,934,468
[45] Date of Patent: Jun. 19, 1990

[54] HOSPITAL BED FOR WEIGHING PATIENTS

[75] Inventors: Clement J. Koerber, Sr., Batesville; Howard J. Boyd, Oldenburg, both of Ind.

[73] Assignee: Hill-Rom Company, Inc., Batesville, Ind.

[21] Appl. No.: 367,006

[22] Filed: Jun. 16, 1989

Related U.S. Application Data

[63] Continuation of Ser. No. 138,829, Dec. 28, 1987.

[51] Int. Cl.⁵ .................. G01G 19/52; A61M 1/00
[52] U.S. Cl. .................. 177/144; 128/897; 604/29
[58] Field of Search .................. 177/144; 604/29; 128/897

[56] References Cited

U.S. PATENT DOCUMENTS

| | | |
|---|---|---|
| 3,217,818 | 11/1965 | Engelsher et al. . |
| 4,015,677 | 4/1977 | Silva et al. ............ 177/144 X |
| 4,363,368 | 12/1982 | Paddon et al. . |
| 4,751,754 | 6/1988 | Bailey et al. . |

OTHER PUBLICATIONS

PV Electronic Bed Patient Weighing System, Pielkenrood-Vinitex B.V., Industrieweg 13, Assendeft-The Netherlands.

Stryker brochure: "The Stryker ICU/CCU Bed has the Critical Advantage", it was designed for the Critical Care Unit (4 pages).

Primary Examiner—George H. Miller, Jr.
Attorney, Agent, or Firm—Wood, Herron & Evans

[57] ABSTRACT

A hospital bed has a support frame and a weigh frame mounted on the support frame by load cells. The output of the load cells is summed to provide a reading of the total weight on the weigh frame. The tare weight is subtracted to provide the patient's weight.

6 Claims, 3 Drawing Sheets

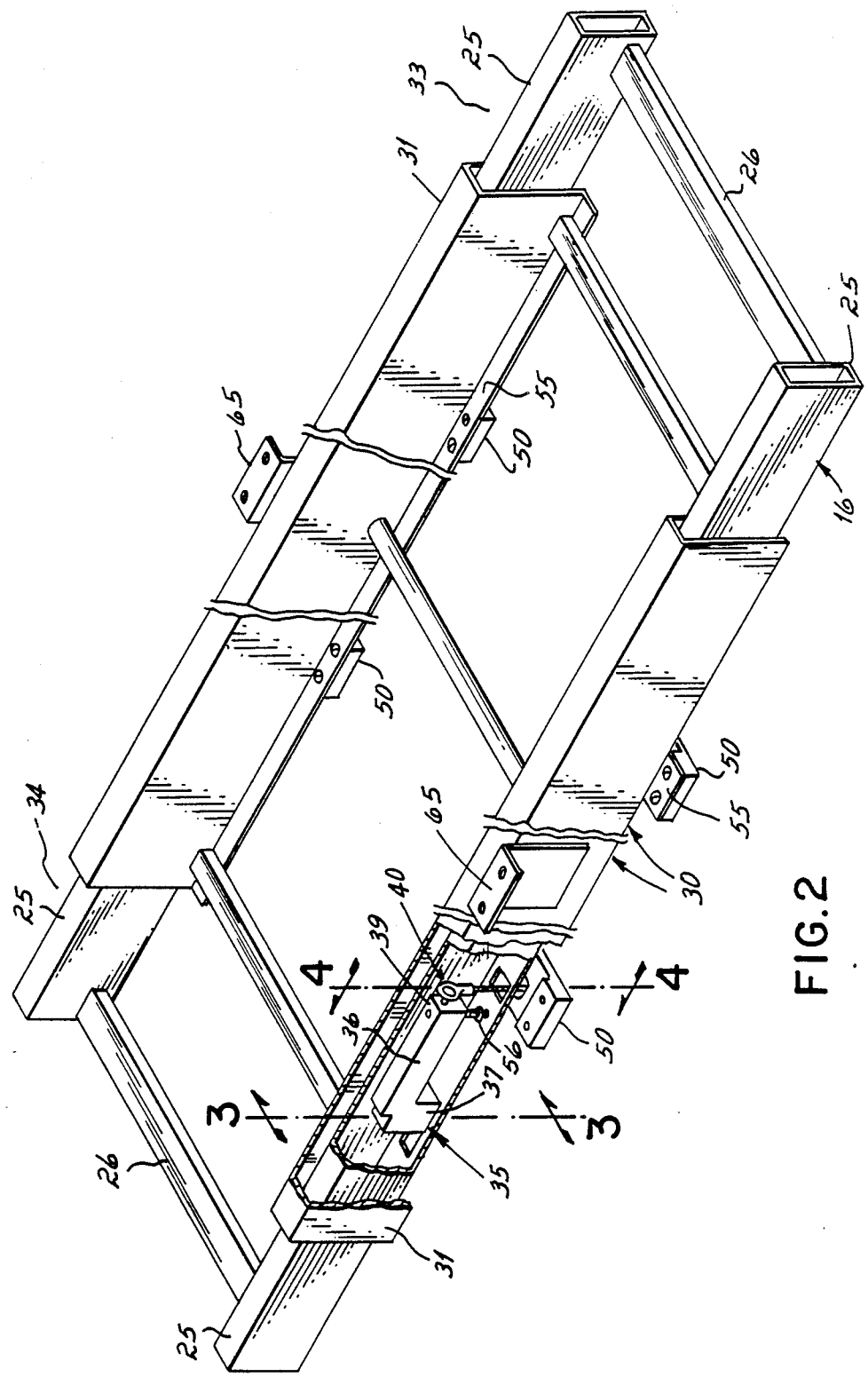

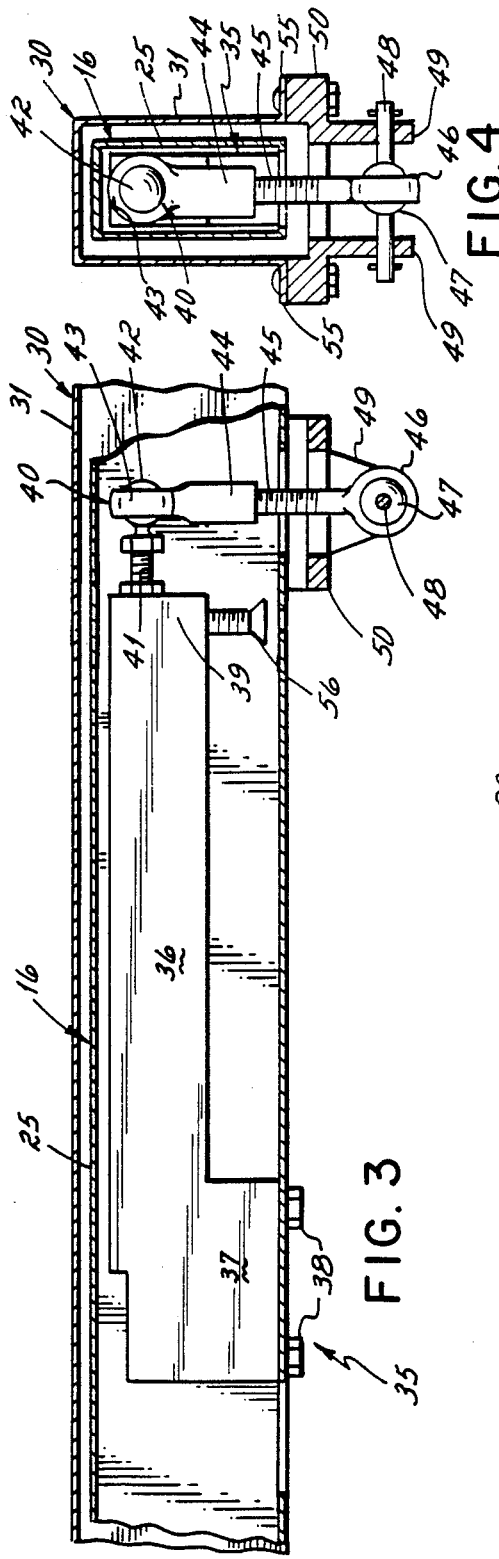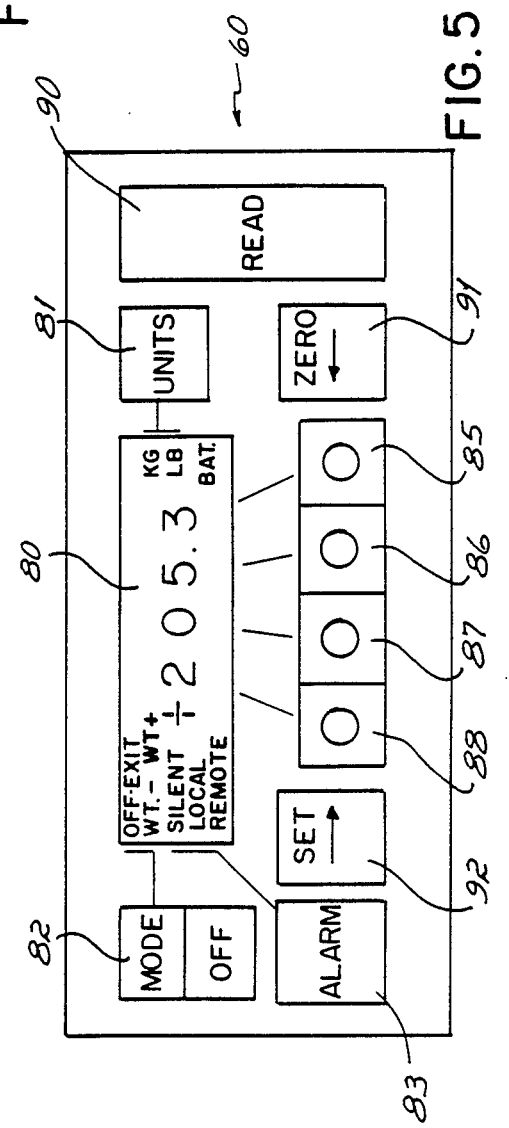

HOSPITAL BED FOR WEIGHING PATIENTS

This is a continuation, of application Ser. No. 07/138,829, filed Dec. 28, 1987.

BACKGROUND OF THE INVENTION

This invention relates to a hospital bed, and more particularly, to a hospital bed having the capability of measuring and maintaining a record of a patient't weight as well as changes in the patient's weight.

The bed of the present invention has its principal use in intensive care or critical care units of a hospital. There, it is necessary to monitor vital functions of a patient on a regular basis. Some must be monitored continuously. One of the vital functions that must be measured on a regular basis is the patient's weight.

Since the patient's health is in such a state that the patient is required to be in intensive or critical care, it is highly likely that the patient cannot leave the bed for a weight measurement and that the patient probably should not be subjected to the trauma attending moving the patient to some sort of scale.

Patient weighing has been done in various ways. A cumbersome sling overlying the bed has been provided, and it has been necessary to move the patient onto the sling and to lift the patient, by means of the sling, off the bed to effect the weighing operation.

Thin weighing scales adapted to be slid under the patient have been disclosed. See U.S. Pat. Nos. 3,217,818 and 3,463,368.

A weigh system forming part of a bed assembly has been disclosed in U.S. Pat. No. 4,015,677. Since there is practically no bed structure disclosed, it is assumed that the total bed and patient are weighed.

It is known that Stryker Corp. of Kalamazoo, Michigan is marketing a bed having a weight monitoring capability, but not much is known about how the weighing is accomplished. The literature indicates that there are provisions for changing tare to accommodate things added or taken from the bed. Aside from the background art heretofore disclosed, there is little art relating to weigh beds.

SUMMARY OF THE INVENTION

The present invention provides an improved weigh bed having the following features:

A weigh frame that contains the patient supporting surface is mounted at its four corners by load cells to a bed support frame. The weight from the four load cells is summed, as will be described below.

Each load cell is fixed at one end to the support frame and at the other to the weigh frame by universal swivels having upper and lower ball joints. Thus, the weigh frame "floats" with respect to the support frame and does not bind, thereby eliminating possible error in the weighing function.

The weigh frame is an inverted U that telescopes over a support frame that is preferably formed of a hollow rectangular section tube. The depending legs of the inverted U provide points of attachment for the connection of the weigh frame to the swivel joint and thus to the support frame. The relationship of inverted U weigh frame and the rectangular tube support frame provides freedom of vertical movement of the weigh frame while restricting horizontal or lateral movement, thus providing a stable support of the weighing assembly with respect to the support frame and lower bed structure.

A four panel patient support surface is mounted entirely on the weigh frame. Pistons and cylinders connect the support surface to the weigh frame to permit normal articulation of the four panels to permit the patient to assume the conventional reclining and sitting attitudes associated with hospital beds. The system for providing pressure to the pistons and cylinders is mounted on the lower base frame and does not form a part of the weight applied to the load cells, with flexible hoses being provided to connect the pressure system to the pistons and cylinders that operate the patient support surface.

The support frame projects at both of its ends beyond the weigh frame. The projecting portions of the support frame carry accessories such as infusion pumps, I.V. bags, drainage bags, head and footboards and the like. By mounting those accessories on the support frame, the adjustments of tare are minimized and the monitoring of the patient's weight is more accurate. For example, with the drainage bag off the weigh frame, the loss of fluids by discharge from the patient into the drainage bag is accurately reflected in loss of patient's weight. Similarly, by mounting the I.V. bag off the weigh frame, increases in the patient's weight by virtue of the introduction of the I.V. fluids is accurately monitored.

The invention provides for changes in tare even when the incremental change in tare is unknown. The invention provides alarm options including an alarm at a remote location such as a nurse's station, an illuminated alarm, an audible alarm and no alarm. The alarms provide notification of the patient's exit from the bed, which is particularly useful for patients whose acuity is impaired. The patient's loss or gain of a predetermined amount of weight can be programmed to operate the alarm. The invention provides for displaying of weight in either pound units or kilogram units. All of the controls for the scale may be battery-operated and the weight control system provides, on its display, an indicator for low battery supply.

BRIEF DESCRIPTION OF THE DRAWINGS

The several features of the invention will become more readily apparent from the following detailed description taken in conjunction with the accompanying drawings in which:

FIG. 2 is a perspective view of the support frame and weigh frame combination;

FIG. 3 is a cross-sectional view taken along lines 3—3 of FIG. 2;

FIG. 4 is a cross-sectional view taken along lines 4—4 of FIG. 2; and

FIG. 5 is a plan view of the display for the control/readout unit associated with the weigh scale.

Figure 1:
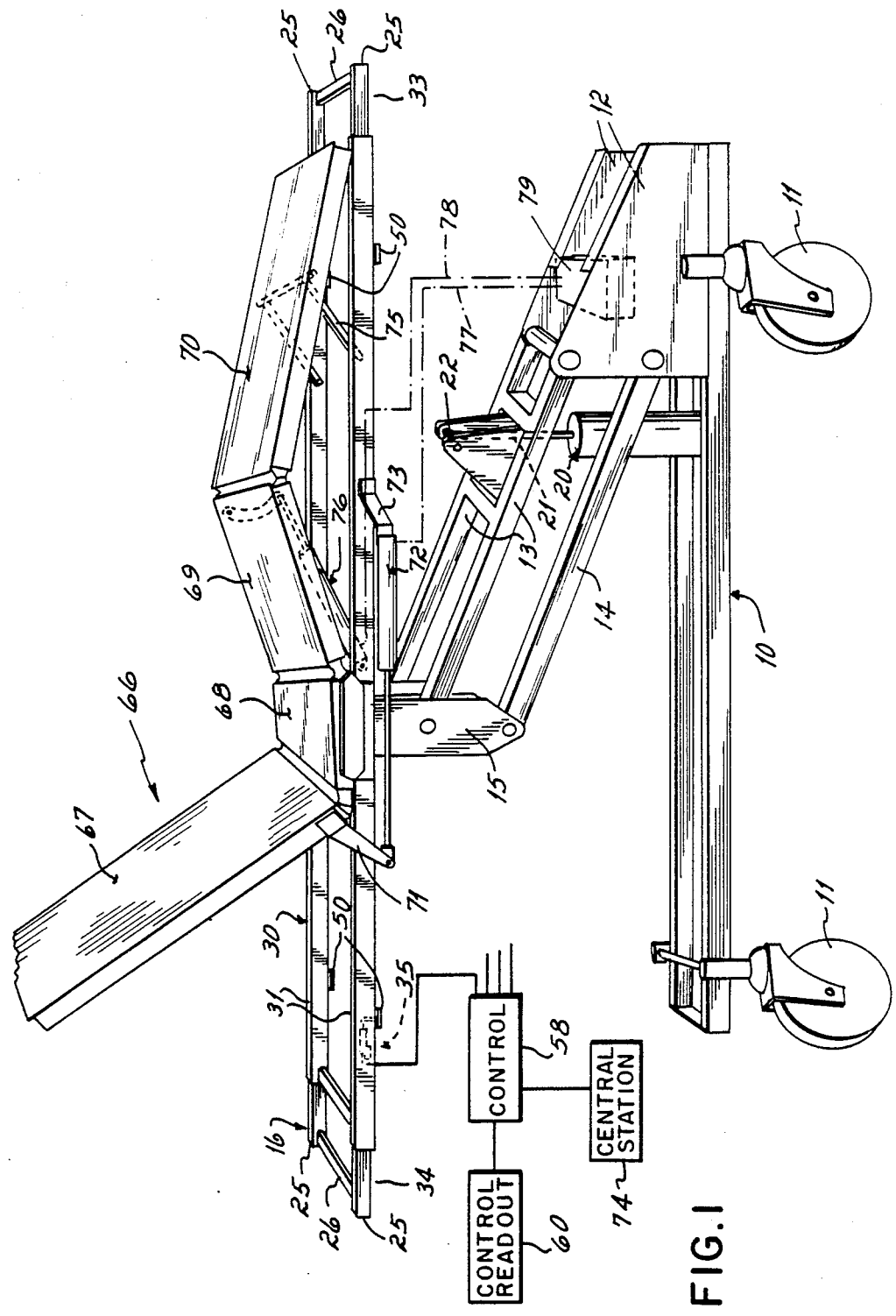
FIG. 1 is a perspective view of a bed employing the present invention.

The bed to which the present invention is applied is shown in FIG. 1. That bed is more fully described and claimed in copending application Ser. No. 7-034,232, filed Apr. 2, 1987. The details of that disclosure are incorporated herein by reference but, except as indicated, do not form a part of the present invention.

The bed has a base frame 10 that is supported on casters 11. Bosses 12 fixed to the base frame pivotally support the ends of a cantilevered support arm 13 and a stabilizer arm 14. The ends of the cantilevered support arms 13 and the stabilizer arm 14 are pivotally connected to a bracket 15, thereby providing a parallelogram linkage support for the bed. The bracket 15 is bolted to support frame 16. A piston and cylinder 20 driving a piston rod 21 is mounted on the base frame 10 with the piston rod 21 being connected to the support arm 13 by means of a clevis mount 22. Actuation of the piston and cylinder 20 causes the piston rod 21 to extend and contract, thereby raising and lowering the parallelogram linkage and the support frame 16 of the bed.

Referring to FIGS. 1–4, the support frame 16 consists of two tubular rectangular section beams 25 joined together by transverse bars 26 mounted at each end of the beams 25. A weigh frame 30 is mounted on the support frame 16. The weigh frame consists of two inverted U-shaped beams 31 that are shorter than the rectangular beams of the support frame. The rectangular beams of the support frame are nested within the U-shaped beams of the weigh frame with front and rear portions 33 and 34 of the support beam projecting beyond the weigh frame 30.

At each corner of the weigh frame 30, the weigh frame is supported on the support frame by a load cell 35. The load cell is an elongated element 36, containing a strain gauge, not shown, and having a boss 37 connected by bolts 38 to the inside of the rectangular beam 25. Thus, the major portion of the load cell is cantilevered from the boss 37 presenting a free end 39. The free end 39 is connected to a swivel 40 by means of a bolt 41 threaded into the free end 39 of the load cell. The projecting end or head of the bolt 41 is a ball 42. The ball sits in a housing 43 to form a ball joint. The housing has a female thread 44 that is connected to a male thread 45 on a second housing 46. The second housing 46 receives a ball 47 to form a second ball joint. The ball 47 is mounted on a pin 48 that is secured to a clevis mount 49 on a bracket 50.

At each corner of the weigh frame flanges 55 project laterally. The brackets 50 are bolted to said flanges 55 across the open end of the U-shaped beams 31. Thus, each swivel mounting securely connects the free end of the load cell to the weigh beam 31. The swivel connection permits limited universal movement of the weigh frame in the horizontal direction, thereby preventing any binding of the weigh frame with respect to the support frame. Preferably, a set screw 56 is provided in free end 39 to limit the movement of the load cell in a downward direction while permitting the load cell to be stressed to the point of reflecting a weigh level well beyond the expected loading of the corner of the weigh frame, thereby preventing damage to the load cell. The load cell is provided with suitable strain gauges configurated into a Wheatstone bridge as is conventional. The strain gauges are connected to a computerized control 58 which in turn is connected to a control/readout unit 60, to be described more fully below. The output of the strain gauges are read sequentially and then summed to provide the total weight on the weigh frame.

The weigh frame has two laterally-projecting brackets 65. A patient support 66 having a head panel 67, a seat panel 68, a thigh panel 69 and a foot panel 70 is secured by means of the seat panel to the brackets 65 and, hence, to the weigh frame. The head panel 67 is hinged to the seat panel 68 and is connected by a bracket 71 to a piston and cylinder 72 which is secured to a bracket 73 on the weigh frame. Thus, the piston and cylinder 72 on the weigh frame causes the raising and lowering of the head panel 67.

The foot panel 70 is pivotally connected to a bracket 75 which is pivoted to the weigh frame. The foot panel is hinged to the thigh panel 69 which is in turn pivoted to the seat panel. A piston and cylinder 76 connects the thigh panel to the weigh frame. The pistons and cylinders 72 and 76 are connected by hoses, diagrammatically indicated at 77 and 78, to a hydraulic system 79 mounted on the base frame. The manipulation of the panels of the patient support and manipulation of the support frame are all performed in a manner as described in said copending application Ser. No. 7-034,232 and forms no part of the present invention except to note the pistons and cylinders for operating the patient support panels are mounted on the weigh frame and become a part of its tare whereas the hydraulic system including pump and fluid reservoir is mounted on the main frame with only hoses being connected between the two. It should be understood that the manipulation of said panels could be performed using electric motors mounted on the weigh frame and a power source mounted on the base, with conductors connecting the power source to the weigh frame.

The portions 33 and 34 of the support frame that project beyond the weigh frame provide elements directly connected to the main frame for supporting accessories such as infusion pumps, I.V. bags, drainage bags, headboards and the like. All of those accessory elements are thus supported separately from the weigh frame and the weighing system.

The bed as thus described will be outfitted with a mattress, sheets, pillows, blankets, and the like. These items become part of the tare. When these are varied, as by adding a blanket or removing pillow, the tare can be changed, whether the weight of the items be known or unknown, by following an easy sequence of steps on the control/readout unit 60. Further, an attendant can set the controls to provide an alarm, visual or audible, to warn an attendant that the patient has lost or gained weight beyond predetermined limit, or that the patient has left the bed. Since I.V. bags and drainage bags are supported on the support frame 16 and/or bracket 15 and are thus out of the weighing system, losses from the I.V. bags and gains in the drainage bag do not influence the determination of the patient's true weight.

The alarm is adapted to be connected to a central nurse station 74 so as to initiate an immediate response to an emergency situation such as a patient's falling or climbing out of bed; or a delayed response for weight gain or loss beyond the pre-set limit.

The control/readout unit 60 is preferably mounted on the front or foot end of the bed convenient for reading and manipulating by the attendant.

The panel has a liquid crystal display 80 that will display the numbers indicating the weight and will display the weight units as KG or LB. The units, KG or LB, are set by the units key 81. The display will also show one of four modes: OFF, EXIT, WEIGHT (+), WEIGHT (−). The monitoring mode is selected by mode key 82. The display will also show the alarm which is one of three alternatives: silent, local, remote. The alarm condition is determined by the alarm key 83. Four digits are displayed to reflect weight. These digits are controlled by four digit stepping keys: 85 for tenths, 86 for units, 87 for tens and 88 for hundreds. The hundreds key sequences the display through 0, 100, 200, 300, 400, −400, −300, −200, −100, −0, +0. Thus, by proper sequencing of the hundreds key, the units can be changed from plus to minus.

A read key 90 is provided to activate a weight reading. A zero key 91 is provided to activate a tare reading or effect tare adjustments and a set key 92 is provided to activate monitoring controls. The key functions are set forth more particularly as follows:

READ Initiates 5 to 8 sec weight measurement upon release. Causes display "+" and preset units, either LB or KG, as previously set, to blink upon closure and while measurement is in process. Signals measurement display with a chime.

UNITS Always comes up in previously set units. Alternately displays in LB or KG upon contact closure. Freezes display when activated and held during weight display. Resets 10 sec. display-hold-timer upon contact opening.

ZERO *Initiates automatic zero-tare of empty bed when held while touching READ. *Activates digit stepping keys for entry of known tare change, plus or minus, when held. *Increments total tare value by difference between display and memory, when activated and held during display while then touching READ. Recalls total system tare value when activated and held; displays for 10 sec after release, or until cancelled by READ or SET. *All tare operations are protected from accidental change by dual-key or sequenced operation.

SET Activates display when held, to show existing alarm weight value for monitoring modes. Activates digit stepping keys when held, to allow setting or changing existing alarm weight value. Facilitates MODE and ALARM setup when held, by activating display when display is otherwise inactive. Releasing SET causes display to clear. Provide memory recall of last weight when held while activating READ.

MODE/OFF Selects monitoring mode, shown in display, and as described:

OFF: Automatically timed monitoring functions inactive.

EXIT: Rough weight measurement (+0, −10% accuracy) taken every 3 to 4 seconds. Places EXIT alarm if weight falls below existing alarm-weight value for two successive readings.

WT−: Precise weight measurement (±1% accuracy, ±0.1% repeatability) taken every 10 minutes. Places weight-loss alarm if weight falls below existing alarm-weight value for two successive readings. Last weight value is stored in memory for recall.

WT+: Precise weight measurement (±1% accuracy, ±0.1% repeatability) taken every 10 minutes. Places weight-gain alarm if weight exceeds existing alarm-weight value for two successive readings. Last weight value is stored in memory for recall.

Cancels alarm with single touch; requires resetting, as before, to re-arm monitoring mode.

Sequences through available settings in rotation with each touch, or rolls at a ½ sec. rate if held for 1 sec. Skips settings that are not available due to hard-wire inhibit or programmed inhibit. Settable any time a full display is present, that is, during weight display holding time, during total tare display holding time, or any time SET is held activated.

ALARM Selects alarm type, shown in the display, and as described:

SILENT: Flashing yellow LED on Nurse Panel Facade.

LOCAL: Flashing yellow LED plus audio beep from Nurse Panel.

REMOTE: Flashing yellow LED plus room-cancellable call with identifying audio beep transmitted through SIDECOM to nurse station.

During all alarms the preset monitoring condition (EXIT, WT−, or WT+) flashes in the display to identify the type of alarm placed.

Audio tone for EXIT is 400 Hz gated ON for ½ sec., OFF for ½ sec., for WT+ and WT−, a 400 Hz tone gated ON for ½ sec., OFF for 1½ sec. The LED and DISPLAY flash at the same ON/OFF rate as the audio.

Yellow alarm LED burns steadily anytime a monitoring mode has been set; then flashes upon alarm.

Sequences through rotation from SILENT to LOCAL to REMOTE to SILENT with each touch of the key, or rolls at a ½ second rate if held for 1 second.

Settable any time a full display is present, that is, during weight display holding time, during total tare display holding time, or anytime SET is held activated.

Alarm placement occurs within ten seconds if the set weight, when entered, is already in the alarm condition when the SET key is released. This alerts the staff while still in the room.

DIGIT Four (4) digit stepping keys, each
KEYS associated with a single decade numeral of the display, are used to increment the display for ZERO and SET, when either of the latter keys are held.

Dual key activation reduces the opportunity for accidental changes in tare resulting from touching a wrong key.

Hundreds sequence is +0, +1, +2, +3, +4, −4, −3, −2, −1, −0, etc; tens, units and tenths step incrementally from 0 to 9 and then jump back to zero without a carryover into the next decade.

Digits step with each touch of the key, or roll at a ½ second rate if held more than 1 second.

BAT Annunciator flashes in display when charge is within 5 to 15% of depletion. Scale is fully functional yet with this reserve, and meets all accuracy requirements. Automatically places a nurse call every 10 minutes when BAT display is activated.

NOTE: In tare or recall operations involving holding ZERO or SET while momentarily activating READ, there will be a tendency to release simultaneously. To prevent activation of an unintentional function when READ is released last, controls are designed such that if READ opens last, but within ½ sec. of ZERO or SET opening, the operation will not be affected.

The steps in the various procedures for weighing the patient, changing the tare, changing the alarm, etc., are as follows:

| PROCEDURE | STAFF ACTION | DISPLAY | "M/A and "U" designate "MODE, ALARM and UNITS" |
|---|---|---|---|
| ZERO EMPTY BED | HOLD ZERO | M/A U +T.SY.T$_i$ | TOTAL SYSTEM TARE, INITIAL (T.SY.T.$_i$) is displayed as long as ZERO is held. |
|  | TOUCH READ | M/A U | Display changes to Zero to indicate |

-continued

| PROCEDURE | STAFF ACTION | DISPLAY | "M/A and "U" designate "MODE, ALARM and UNITS" |
|---|---|---|---|
| | | +000.0 | procedure when READ closes with ZERO held. |
| | RELEASE ZERO | +000.0 U | Display blinks during 5-8 sec. zero tare measurement. Blinking and measurement start upon release of ZERO. |
| | | CHIME | CHIME signals completion of tare measurement. |
| | | M/A U +T.SY.T.$_f$ HOLDS 10 sec. | TOTAL SYSTEM TARE, FINAL (T.SY.T.$_f$) to Zero bed, is stored in memory. DISPLAY holds 10 sec. or until cancelled by SET or READ. UNITS change converts display on closure; restarts 10 sec. timer on release. MODE and ALARM may be set during display. |
| READ SYSTEM TARE | TOUCH ZERO | M/A U +T.SY.T. HOLDS 10 Sec. | TOTAL SYSTEM TARE is displayed upon ZERO closure and holds for 10 sec. after release, or until cancelled by READ or SET. UNITS change converts display on closure; restarts 10 sec. timer on release. MODE and ALARM may be set during display. |
| INPUT KNOWN TARE | HOLD ZERO | M/A U +T.SY.T.$_i$ | TOTAL SYSTEM TARE, INITIAL is displayed upon ZERO closure. |
| | CHECK UNITS | | DISPLAY converts if UNITS are changed. |
| | INPUT EXACT TARE CHANGE DIGIT STEPPING KEYS ADDED (+) OR REMOVED (−) | M/A U ±ΔT | DISPLAY numerals clear with first key entry to show ΔT input. DISPLAY increments with each key touch; rolls upward at ½ sec. per step without decade carryover if digit stepping key is held for 1 sec. Hundreds digit rolls +0, +1, +2, +3, +4, −4, −3, −2, −1, −0, etc. |
| | RELEASE ZERO | M/A U +T.SY.T.$_f$ | TOTAL SYSTEM TARE, FINAL (T.SY.T.$_f$ = T.SY.T$_i$ + ΔT), which includes the known tare change, ±ΔT, is displayed 10 sec. after release, or until cancelled by READ or SET. UNITS change converts display on closure; restarts 10 sec. timer on release. MODE and ALARM may be set during display. |
| INPUT UNKNOWN TARE | TOUCH READ, (OR USE VALUE IN MEMORY WITHOUT NECESSITY OF RECALL) | + U | Display blinks during 5 to 8 sec. weight measurement. Blink starts with READ closure; measurement, upon release. |
| | | CHIME | CHIME signals completion of PATIENT WEIGHT measurement. |
| | | M/A U +P.W. HOLDS 10 Sec. | PATIENT WEIGHT is displayed for 10 secs. or until cancelled by READ or SET, at which time it bumps into memory. UNITS change converts display on closure; restarts 10 sec. timer on release. MODE and ALARM may be set during display. |
| | CHANGE BED TARE | | Time to complete equipment or bed change is not critical. |
| | TOUCH READ | + U | Display blinks during 5 to 8 sec. weight measurement. Blink starts with READ closure; measurement, upon release. |
| | | CHIME | CHIME signals completion of PATIENT PLUS UNKNOWN TARE WEIGHT measurement. |
| | | M/A U +P + ΔT HOLDS 10 Sec. | PATIENT PLUS UNKNOWN TARE is displayed for 10 sec., or until cancelled by READ or SET. UNITS may still be changed, converting display on closure, restarting 10 sec. timer on release. |

-continued

| PROCEDURE | STAFF ACTION | DISPLAY | "M/A and "U" designate "MODE, ALARM and UNITS" |
|---|---|---|---|
| | | | MODE and ALARM may be set during display without having an effect on the procedure. |
| | DURING DISPLAY HOLD ZERO TOUCH READ | M/A U +P.W. | DISPLAY converts upon closure, to initial PATIENT WEIGHT from memory. TARE increment, $\Delta T = (P + \Delta T) - (P.W.)$, is added to TOTAL SYSTEM TARE and displayed upon closure of READ |
| | RELEASE ZERO | M/A U +T.SY.T.$f$ HOLDS 10 Sec. | ADJUSTED TOTAL SYSTEM TARE, including tare change $\Delta T$, is displayed 10 sec. after release, or until cancelled by READ or SET. UNITS change converts display on closure; restarts 10 sec. timer on release. MODE and ALARM may be set during display. |
| WEIGH PATIENT | TOUCH READ | + U | DISPLAY blinks "+" and "KG" or "LB", as previously set, during 5 to 8 sec. weight measurement. Blink starts with READ closure; measurement, upon release. |
| | | CHIME | CHIME signals completion of PATIENT WEIGHT measurement. |
| | | M/A U +P.W. HOLDS 10 Sec. | PATIENT WEIGHT is displayed for 10 sec., or until cancelled by READ or SET, at which time it bumps into memory. |
| | TOUCH UNITS | RESTARTS 10 Sec. | UNITS change converts display on closure; restarts 10 sec. timer on release. MODE and ALARM may be set during display. |
| HOLD DISPLAY | HOLD UNITS RELEASE UNITS | M/A U +P.W. HOLDS 10 Sec. | Units system will change with first touch; change back with second operation; will hold indefinitely if switch is held activated. DISPLAY holds 10 sec. after release, or until cancelled by READ or SET. |
| MEMORY RECALL | HOLD SET | M/A U ±AL'M.WT | Existing alarm weight value is displayed including ALARM and MODE status and weight UNITS. DISPLAY converts if UNITS are changed. |
| | ACTIVATE READ | M/A U +P.W. | DISPLAY converts upon closure, to last value of weight bumped into memory during weight measurement or automatic monitoring mode (WT+ or WT−) |
| | RELEASE READ | M/A U ±AL'M WT | DISPLAY converts back to existing alarm weight value. |
| | RELEASE SET | | DISPLAY disappears instantly; weighing cycle is not initiated. |
| MONITORING SETUP | HOLD SET | M/A U ±AL'M WT | Existing alarm weight value is displayed, including ALARM and MODE status and weight UNITS |
| | SET MODE: EXIT WT−, WT+, or OFF | M/A U ±AL'M WT | MODE setting steps sequentially with each touch of the key, whenever display is present, or will roll at ½ sec. per step if held for 1 sec. |
| | SET ALARM: SILENT LOCAL, or REMOTE | M/A U ±AL'M WT | ALARM setting steps sequentially with each touch of the key, whenever display is present, or will roll at ½ sec. per step if held for 1 sec. |
| | CHECK UNITS | M/A U ±AL'M WT | DISPLAY converts if units are changed. |
| | ENTER ALARM WEIGHT | M/A U ±AL'M WT | DISPLAY increments with each key touch; rolls upward at ½ sec. per step without decade carryover if digit stepping key is held for 1 sec. Hundreds digit rolls +0, +1, +2, +3, +4, −4, −3, −2, −1, −0, +0 etc. |
| (RECALL MEMORY DURING SETUP) | ACTIVATE READ | M/A U +P.W. | DISPLAY converts upon closure, to last value of weight bumped into memory during weight measurement |

-continued

| PROCEDURE | STAFF ACTION | DISPLAY | "M/A and "U" designate "MODE, ALARM and UNITS" |
|---|---|---|---|
| | | | or automatic monitoring mode (WT− or WT+) |
| | RELEASE READ | M/A U ±AL'M WT | DISPLAY converts, upon release, back to ALARM WEIGHT value |
| | RELEASE SET | | After MODE, ALARM, and ALARM WEIGHT settings have been completed (in any sequence), releasing SET blanks DISPLAY instantly. |
| RECALL ALARM WT | HOLD SET | M/A U ±AL'M WT | Existing ALARM WEIGHT value is displayed, including ALARM and MODE status and preset weight UNITS. |
| | RELEASE SET | | DISPLAY blanks instantly. |
| SHUT OFF ALARM | TOUCH MODE | M | MODE setting blinks in display when alarm occurs; alarm clears with single touch of MODE key. To reset, condition must be cleared and MODE reset as above. |

The control system admits of the possibility of making an initial setting that eliminates the bed tare and the patient's weight. Thus, the display will provide a continuous display of the change in patient's weight.

It will be appreciated that while the preferred embodiment of the invention is described in connection with hospital beds, the invention may be adapted for use in connection with other forms of weigh apparatus, such as patient supporting wheelchairs, livestock scales, or the like.

From the above disclosure of the general principles of the present invention and the preceding detailed description of a preferred embodiment, those skilled in the art will readily comprehend the various modifications to which the present invention is susceptible. Therefore, we desire to be limited only by the scope of the following claims and equivalents thereof:

We claim:

1. In a hospital bed having a weigh frame supported by at least one load cell on a support frame, a control/readout apparatus connected to said load cell comprising:
    a display for weigh data,
    control means including keys for entering weigh units connected between said load cell and said display,
    said control means for entering and displaying tare weight and changing tare when an unknown change in tare occurs, and for displaying the patient's weight, and
    means for initiating an alarm at a central station when a patient leaves said bed.

2. In a hospital bed having a weigh frame supported by at least one load cell on a support frame, a control/readout apparatus connected to said load cell comprising:
    a display for weigh data,
    control means including keys for entering weigh units connected between said load cell and said display,
    said control means for entering and displaying tare weight and changing tare when an unknown change in tare occurs, and for displaying the patient's weight,
    a SET switch for activating said display to show alarm weight and to activate keys for setting or changing existing alarm weight value,
    and a MODE switch for sequencing said control means through "exit" weight, "over" weight, and "under" weight,
    and an alarm that is activated when any of said preset mode conditions occur.

3. In a hospital bed having a weigh frame supported by at least one load cell on a support frame, a control/readout apparatus connected to said load cell comprising:
    a display for weigh data,
    control means including keys for entering weigh units connected between said load cell and said display,
    said control means for entering and displaying tare weight and changing tare when an unknown change in tare occurs, and for displaying the patient's weight, and
    means for initiating an alarm at a central station when a patient leaves said bed,
    an ALARM switch for programming the following alarm types:
    Silent: flashing LED on readout unit
    Local: flashing LED plus audio beep on readout unit
    Remote: audio beep transmitted to central station.

4. In a weigh apparatus having a weigh frame supported by at least one load cell on a support frame, a control/readout apparatus operatively connected to said load cell and comprising:
    a display for weigh data,
    control means including keys for entering weigh units connected between said load cell and said display,
    said control means for entering and displaying tare weight and changing tare when an unknown change in tare occurs,
    and for displaying the weight of a load supported by said weigh frame, and
    means for initiating an alarm at a central station when a load is removed from said weigh frame.

5. In a weigh apparatus having a weigh frame supported by at least one load cell on a support frame, a control/readout apparatus operatively connected to said load cell and comprising:
    a display for weigh data,
    control means including keys for entering weigh units connected between said load cell and said display,
    said control means for entering and displaying tare weight and changing tare when an unknown change in tare occurs,
    and for displaying the weight of a load supported by said weigh frame,
    a SET switch for activating said display to show alarm weight and to activate keys for setting or changing existing alarm weight value, a MODE switch for sequencing said control means through "exit" weight, "over" weight, and "under" weight, and an alarm that is activated when any of said preset mode conditions occur.

6. In a weigh apparatus having a weigh frame supported by at least one load cell on a support frame, a control/readout apparatus operatively connected to said load cell and comprising:

a display for weigh data, control means including keys for entering weigh units connected between said load cell and said display, said control means for entering and displaying tare weight and changing tare when an unknown change in tare occurs, and for displaying the weight of a load supported by said weigh frame, means for initiating an alarm at a central station when a load is removed from said weigh frame, and an ALARM switch for programming the following alarm types:

Silent: flashing LED on readout unit
Local: flashing LED Plus audio beep on readout unit
Remote: audio beep transmitted to central station.

* * * * *

UNITED STATES PATENT AND TRADEMARK OFFICE
CERTIFICATE OF CORRECTION

PATENT NO.   : 4,934,468

DATED        : June 19, 1990

INVENTOR(S)  : Clement J. Koerber, Sr. and Howard J. Boyd

It is certified that error appears in the above-identified patent and that said Letters Patent is hereby corrected as shown below:

Face of patent, [63], "Continuation" should be

-- Division --

Column 1, line 1, "continuation" should be -- division -- .

Signed and Sealed this

Seventh Day of January, 1992

Attest:

HARRY F. MANBECK, JR.

*Attesting Officer*      *Commissioner of Patents and Trademarks*